United States Patent [19]

Mardiguian

[11] 4,112,000
[45] Sep. 5, 1978

[54] TERPENOPHENOLS

[75] Inventor: Jean Mardiguian, Paris, France

[73] Assignee: MAR-PHA, Societe d'Etude et d'Exploitation de Marques, France

[21] Appl. No.: 803,511

[22] Filed: Jun. 6, 1977

Related U.S. Application Data

[62] Division of Ser. No. 566,364, Apr. 9, 1975, Pat. No. 4,067,899.

[30] Foreign Application Priority Data

Apr. 11, 1974 [GB] United Kingdom ............... 16142/74

[51] Int. Cl.² ..................... C07C 39/27; A61K 31/055
[52] U.S. Cl. ............................... 568/734; 260/465 R; 260/613 R; 424/347
[58] Field of Search ..................................... 260/619 D

[56] References Cited

U.S. PATENT DOCUMENTS

| | | | |
|---|---|---|---|
| 2,221,809 | 11/1940 | Mills ................................. | 260/619 D |
| 2,289,550 | 7/1942 | Roblin et al. ..................... | 260/619 D |
| 2,524,086 | 10/1950 | Schmerling ..................... | 260/619 D |
| 2,537,647 | 1/1951 | Kitchen ........................... | 260/619 D |
| 3,833,671 | 9/1974 | Mardiguian et al. ............. | 260/619 D |
| 3,878,254 | 4/1975 | Gazare .............................. | 260/619 D |

Primary Examiner—Joseph E. Evans
Attorney, Agent, or Firm—Bucknam and Archer

[57] ABSTRACT

New terpenophenols of the general formula:

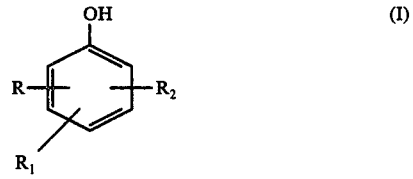

wherein

R is a 2-isobornyl, 5-camphyl or 2-norbornyl group of exo or endo configuration and in the ortho, meta or para position with respect to the OH group; $R_1$, $R_2$ may each be a hydrogen atom or halogen atom (Cl, Br, F,I) or a lower alkyl or lower alkoxy radical having a straight or branched chain of 1 to 4 carbon atoms or a nitro or cyano group.

4 Claims, No Drawings

TERPENOPHENOLS

This is a division, of application Ser. No. 566,364, filed Apr. 9, 1975, now U.S. Pat. No. 4,067,899.

The present invention relates to new terpenophenols of the general formula:

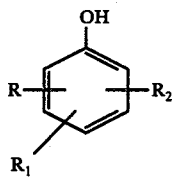

in this formula:
R is a terpene radical chosen from the following group:

2-isobornyl (2)

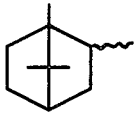

5-camphyl (5)

2-norbornyl (2)

of exo or endo configuration and in the ortho, meta or para position with respect to the OH group.

$R_1$, $R_2$ may each be a hydrogen atom or halogen atom (Cl, Br, F, I) or a lower alkyl or lower alkoxy radical having a straight or branched chain of 1 to 4 carbon atoms or a nitro or cyano group.

More particularly:

R is in the 2, 3 or 5 position of the phenol ring, $R_1$ is a hydrogen atom or halogen atom, in particular Cl or Br, or a nitro, cyano group or a lower alkyl or lower alkoxy radical having 1 to 4 carbon atoms, in position 4 of the phenol ring.

$R_2$ is a hydrogen atom or a lower alkyl radical of 1 to 4 carbon atoms.

Advantageously, it is possible to prepare the terpenophenols of formula (I) in which $R_1$ is an atom of bromine by direction bromination of a corresponding terpenophenol (formula I, $R_1$ = H) by means of a bromine-dioxan complex, in particular dioxan dibromide, preferably in an ethyl ether medium, under cold conditions, at a temperature less than or equal to the ambient temperature in particular from 0° to 10° C.

Advantageously, it is possible to prepare the terpenophenols of formula (I) in which $R_1$ is a chlorine atom, by chlorination of the methyl ether of a corresponding terpenophenol (formula I, $R_1$ = H) by means of phosphorus pentachloride, followed by demethylation of the resulting product. Demethylation may advantageously take place by means of red phosphorus in hydriodic acid.

These new phenols have interesting bacteriostatic properties and are useful in the treatment of infections by gram + ve and gram − ve bacteria. The following examples are given to illustrate the invention without limiting the scope thereof.

EXAMPLE 1

2-isobornyl-4-nitro-5-methylphenol 0.7 $cm^3$ of nitric acid (density 1.42g/$cm^3$) are added dropwise to a solution, cooled to 15° C, of 2.4g of 2-isobornyl-5-methyl phenol dissolved in 15 $cm^3$ of acetic acid. After the addition, the temperature of the reaction mixture is maintained at 15° to 17° C for 3 hours then the mixture is left overnight at ambient temperature. The mixture is poured on crushed ice, which is then extracted with ether, the ethereal phase is washed with sodium carbonate and then with water. After evaporation under reduced pressure, a dark red viscous mass is obtained which is dissolved in an 8:2 mixture of benzene/methanol and chromatographed on a silica gel column with the same mixture of solvents. There is thus obtained 0.8g of product which is crystallised from cyclohexane. The pale yellow product obtained has a melting point of 184°–186° C.

ANALYTICAL CHARACTERISTICS

Analysis for $C_{17}H_{23}NO_3$ (M.W. = 289)

|  | C | H | N |
|---|---|---|---|
| Calculated (%) | 70.56 | 8.01 | 4.8 |
| Found (%) | 70.50 | 8.2 | 4.7 |

INFRA-RED SPECTRA

As a dispersion in KBr, the characteristic absorption bands are as follows:

| OH | 3360 $cm^{-1}$ |
|---|---|
| $NO_2$ | 1530, 1320, 870, 640 |
| Aromatic nucleus | 1625, 1580, 1490 |
| isobornyl | 2950, 2890 |

NUCLEAR MAGNETIC RESONANCE SPECTRA

The following peaks are observed for a solution in deuterated chloroform, using tetramethyl silane (TMS) as reference.

| $CH_3$ | (bridge head) | 0.75 ppm | singlet |
|---|---|---|---|
| $CH_3$ | geminal | 0.8 and 0.82 ppm | singlets |
| $CH_3$ | aromatic | 2.55 ppm | singlet |
| $CH_3$ | bornane ring | 1.65 ppm | massive |
| —C—H | (exo) | 3.15 ppm | triplet |
|   | aromatic | 6.7 and 8.1 ppm | singlets |
| OH |  | 5.8 ppm |  |

EXAMPLE 2

2-isobornyl-4-bromo-5-methyl-phenol 3.06g of the dibromide of dioxan were added slowly with stirring to a solution, cooled to 5° C, of 30g of 2-isobornyl-5-methyl-phenol in 200 $cm^3$ of ethyl ether, whilst ensuring that the temperature of the reaction mixture does not exceed 10° C. After the addition, the mixture is allowed to return to ambient temperature and left overnight. The organic phase is washed successively with an aqueous solution of sodium chloride, 10% sodium bicarbonate and finally water.

After drying and evaporation of the ether, the residue is crystallised in pentane then in iso-octane and 21.4g of pure product are obtained (m.pt. 89°-90° C).

ANALYTICAL CHARACTERISTICS

Analysis for $C_{17}H_{23}OBr$ (M.W. = 322.9)

|  | C | H | Br |
|---|---|---|---|
| Calculated (%) | 63.18 | 7.12 | 24.74 |
| Found (%) | 63 | 7.2 | 24.5 |

I.R. SPECTRA

The following characteristic bands are observed with a 0.1 M solution in $CCl_4$:

| free OH | 3.600 cm$^{-1}$ |
|---|---|
| aromatic nucleus | 1615, 1505 |
| isobornyl | 2850, 2880, 1470-1460 |

N.M.R. SPECTRA

The following peaks are observed with a solution in deuterated chloroform (TMS reference):

| $CH_3$ | Bridge head | 0.78 ppm | singlet |
|---|---|---|---|
| $CH_3$ | geminal | 0.82 and 0.85 ppm | singlets |
| $\|$ | (exo) | 3.03 ppm | triplet |
| —C—H | aromatic | 6.6 and 7.4 ppm | singlets |
| $\|$ |  |  |  |
| H |  |  |  |
| OH |  | 4.7 ppm |  |

EXAMPLE 3

2-isobornyl-4-nitrophenol 5.1 cm$^3$ of nitric acid ($d$ = 1.42) are added dropwise to a solution, cooled to 15° C, of 18.4g of O-isobornyl-phenol in 60 cm$^3$ of acetic acid. After addition, the temperature of the reaction mixture is maintained at 15° to 17° C for 5 hours and then the mixture is poured onto crushed ice. It progressively forms a red viscous mass which is extracted, after separation of the aqueous phase, with 350 cm$^3$ of ethyl ether. The ethereal solution is washed copiously with water than with 5% soda.

The alkaline phase is acidified and extracted with ether. After evaporation of the solvent and crystallisation of the residue in petroleum ether (b.pt. 40°-65°), 10.5g of brown product are obtained (m.pt. 180°-182° C).

ANALYTICAL CHARACTERISTICS

Analysis for $C_{16}H_{21}NO_3$ (M.W. = 275)

|  | C | H | N |
|---|---|---|---|
| Calculated (%) | 69.79 | 7.69 | 5.09 |
| Found (%) | 69.88 | 7.64 | 4.75 |

I.R. SPECTRA

In dispersion in KBr the following characteristic bands are observed:

| $NO_2$ | 1520, 1335, 860, 650 cm$^{-1}$ |
|---|---|
| OH | 3360 |
| aromatic nucleus | 1620, 1590, 1485 |

| isobornyl | 2880-2950, 1460-1470 |
|---|---|

N.M.R. SPECTRA

The following major peaks are observed with a solution in deuterated chloroform (TMS reference):

| $CH_3$ | bridge head | 0.8 ppm | singlet |
|---|---|---|---|
| $CH_3$ | geminal | 0.88 and 0.9 ppm | singlets |
| $\|$ | (exo) | 3.15 ppm | triplet |
| —C—H |  | 5.8 ppm |  |
| $\|$ |  |  |  |
| OH |  |  |  |

EXAMPLE 4

2-isobornyl-4-bromophenol 10.8g of the dibromide of dioxane are added slowly with stirring to a solution, cooled to 5° C, of 10g of o-isobornyl-phenol in 100 cm$^3$ of ethyl-ether while maintaining the temperature of the reaction between 5° and 10° C. After addition, the reaction mixture is allowed to reach ambient temperature and left overnight. Then the mixture is washed successively with a solution of sodium chloride, a 10% solution of sodium bicarbonate then with water. The organic phase is dried and the ether evaporated. The residue is distilled under reduced pressure. The fraction which passes over at 183° C (at 3 mm Hg) is collected. By crystallisation in iso-octane, there is obtained 9g of pure, white, product, (m.pt. = 81° C).

ANALYTICAL CHARACTERISTICS

Analysis for $C_{16}H_{21}OBr$ (M.W. = 308.9)

|  | C | H | Br |
|---|---|---|---|
| Calculated (%) | 62.15 | 6.80 | 25.86 |
| Found (%) | 62.2 | 6.7 | 25.6 |

I.R. SPECTRA

In dispersion in KBr, the following characteristic bands are noted:

| free OH | 3560 cm$^{-1}$ |
|---|---|
| aromatic nucleus | 1600, 1500, 890, 820 |
| isobornyl | 2880, 2950, 1470, 1480 |

N.M.R. Spectra

The following main peaks are observed with a solution in deuterated chloroform (TMS reference)

| $CH_3$ | bridge head | 0.75 ppm | singlet |
|---|---|---|---|
| $CH_3$ | geminal | 0.8 and 0.82 ppm | singlets |
| $\|$ | (exo) | 3.05 ppm | triplet |
| —C—H |  |  |  |
| $\|$ |  |  |  |
| OH |  | 4.6 ppm |  |

EXAMPLE 5

2-exo-norbornyl-4-nitrophenol 3.8 ml. of nitric acid ($d = 1.42$) were added dropwise to a solution, cooled to 15° C, of 9.4g of o-exo-norbornylphenol in 20 cm³ of acetic acid. After the addition the temperature of the reaction mixture is maintained at 15° - 17° C for 3 hours, and is then left for 3 days at a temperature of 5° C. The mixture is then poured on crushed ice, the aqueous phase is decanted and the precipitated brown viscouse mass is extracted with ether. The solvent is removed under reduced pressure and crystallization of the residue in cyclohexane gives 2.4g of pure, grey-white, product (m.pt. 134° - 136° C).

ANALYTICAL CHARACTERISTICS

Analysis for $C_{13}H_{15}NO_3$ (M.W. = 233)

|  | C | H | N |
|---|---|---|---|
| Calculated (%) | 66.93 | 6.48 | 6.01 |
| Found (%) | 66.88 | 6.50 | 5.90 |

I.R. SPECTRA

In dispersion of KBr, the following characteristic absorption bands are noted:

| | |
|---|---|
| $NO_2$ | 1520, 1330, 650 cm$^{-1}$ |
| OH | 3360 cm$^{-1}$ |
| aromatic nucleus | 1620, 1590, 1500 |
| norbornyl | 2880, 2960 |

N.M.R. SPECTRA

In deuterated chloroform the following main peaks are observed (TMS reference).

| | | | |
|---|---|---|---|
| —CH$_2$<br>\|<br>—C—H<br>\|<br>OH | (exo) | 1.6 ppm<br>2.9 ppm<br>5.9 ppm | massive<br>triplet |

EXAMPLE 6

2-isocamphyl-4-bromophenol 8.6g of the dibromide of dioxan are added with stirring to a solution, cooled to 5° C, of 8g of O-isocamphylphenol in 50 cm³ of ethyl ether whilst ensuring that the temperature of the reaction media does not exceed 10° C. The mixture is then left to reach ambient temperature and left overnight.

The ethereal phase is washed successively with a solution of sodium chloride, 10% sodium bicarbonate, sodium chloride and finally with water. The organic phase is then dried over magnesium sulphate and the other is removed under reduced pressure. The residue is crystallised in iso-octane and after three crystallisations there is obtained 2g of pure product (m.pt 67° C).

ANALYTICAL CHARACTERISTICS

Analysis for $C_{16}H_{21}BrO$ (M.W. = 309.25)

|  | C | H | Br |
|---|---|---|---|
| Calculated (%) | 62.1 | 6.8 | 25.9 |
| Found (%) | 62.7 | 6.8 | 25.7 |

I.R. SPECTRA

In dispersion of KBr, the following characteristic bands are noted:

| | |
|---|---|
| isocamphyl | 2900, 2950 cm$^{-1}$ |
| aromatic nucleus | 1600, 1500, 820 |
| OH | 3605 (in CC14) |

N.M.R. SPECTRA

In deuterated chloroform, the following peaks are observed (TMS reference).

| | | | |
|---|---|---|---|
| Isocamphyl | CH$_3$ | 0.85 ppm | doublet |
|  | CH$_3$ geminal | 0.9 and 1 ppm | singlets |
| OH | | 5 ppm | |

EXAMPLE 7

2-isobornyl-4-chloro-5-methylphenol

In a three necked flask fitted with a condenser, there is introduced 51.7g (0.2 mole) of 2-isobornyl-5-methylanisole and 41.6g (0.2 mole) of phosphorus pentachloride. The mixture is heated to 110°-115° C for 2 hours, then the phosphorus trichloride formed is distilled at reduced pressure and the reaction mass is poured into iced water. An extraction with ether is undertaken, the organic phase is washed with water until neutral, dried on sodium sulphate and the ether is evaporated. An orange crystalline mass is obtained. By crystallization in ethanol, 44.2g of 2-isobornyl-4-chloro-5-methylanisole are obtained (m.pt 71°-73° C).

A mixture of 0.003 moles of red phosphorus, 18g of a solution of 57% hydriodic acid ($d = 1.70$) acetic acid and 0.04 moles of the product obtained previously, is heated to reflux during 30 minutes and heated at reflux during 17 hours. After reaction, the mixture is filtered on glass wool, dissolved in water and extracted with ether. The organic phase is washed with a solution of sodium carbonate, then water and dried over sodium sulphate. After evaporation of the solvent, there is obtained an oil which is crystallised in pentane then in iso-octane. There is thus obtained 5.3g of pure product (m.pt. = 98°-100° C).

ANALYTICAL CHARACTERISTICS

Analysis for $C_{17}H_{23}ClO$ (M.W. = 278.8)

|  | C | H | Cl |
|---|---|---|---|
| Calculated (%) | 73.4 | 8.3 | 13 |
| Found (%) | 73.6 | 8.25 | 12.8 |

I.R. SPECTRA

In dispersion in KBr, the following characteristic bands are observed:

| | |
|---|---|
| isobornyl | 2880, 2959, cm$^{-1}$ |
| aromatic nucleus | 1615, 1510, 860 |

-continued

| | |
|---|---|
| OH | 3540 |

N.M.R. SPECTRA

The following peaks are observed with a solution in deuterated chloroform (TMS reference):

| CH$_3$ | bridge head | 0.79 ppm | singlet |
|---|---|---|---|
| CH$_3$ | geminal | 0.82–0.88 ppm | singlets |
| CH$_3$ | aromatic | 2.2 ppm | |
| H | aromatic | 6.5 and 7.2 ppm | |
| OH | phenol | 4.5 ppm | |

EXAMPLE 8

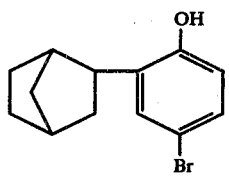

2-EXO-NORBORNYL-4-BROMOPHENOL 53g of dioxan dibromide (0.21 mole) are added slowly for 15 minutes to a solution, cooled to 0° C, of 40g 2-exo-norbornyl phenol (0.21 mole) in 200 cm$^3$ ethyl ester. After stirring at ambient temperature for 1 hour, the ethereal phase is washed successively with a solution of sodium chloride, then a solution of sodium bicarbonate and then with water until neutral. It is then dried on sodium sulphate, evaporated under vacuum and then distilled at reduced pressure. The fraction B.P.$_1$ = 150° C is recovered and 35g of a colourless oil, which forms a mass, are obtained.

ANALYTICAL CHARACTERISTICS

Analysis for C$_{13}$H$_{15}$OBr (M.W. = 267.17)

| | | C | H | Br |
|---|---|---|---|---|
| Calculated | (%) | 58.44 | 5.66 | 29.91 |
| Found | (%) | 58.20 | 5.52 | 29.90 |

I.R. SPECTRA

In the form of a film, the following characteristic bands are noted:

| norbornyl | 2870, 2950, 1475 cm$^{-1}$ |
|---|---|
| OH | 3550, 3440 cm$^{-1}$ |

N.M.R. SPECTRA

The following peaks are observed with a solution in dimethyl sulfoxide (TMS reference):

| norbornyl | endo proton | 2.9 ppm | triplet |
|---|---|---|---|
| | other protons | 1.5 ppm | massive |
| OH | | 9.5 ppm | singlet |
| aromatic nucleus | | 6.7–7.10–7.15 ppm | |

EXAMPLE 9

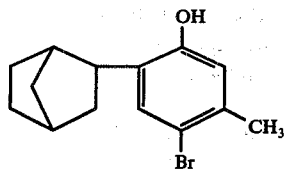

2-EXO-NORBORNYL-4-BROMO-5-METHYL-PHENOL 100g of dioxan dibromide (0.4 mole) are added slowly to a solution, cooled to 0° C, of 80g 2-exo-norbornyl-5-methylphenol (0.4 mole) in 400 cm$^3$ anhydrous ether, whilst ensuring that the temperature does not exceed 5° C. After stirring for 1 hour, the ethereal phase is washed successively with a solution of sodium chloride, then a solution of sodium bicarbonate and then with water until neutral. It is then dried on sodium sulphate and the solvent is evaporated under vacuum. The residue is crystallised in pentane at −20° C. 82g of a pure product are obtained (m.pt = 80° C.)

ANALYTICAL CHARACTERISTICS

Analysis for C$_{14}$H$_{17}$OBr (M.W. = 281.20)

| | | C | H | Br |
|---|---|---|---|---|
| Calculated | (%) | 59.80 | 6.08 | 28.42 |
| Found | (%) | 59.91 | 6.00 | 28.57 |

I.R. SPECTRA

In dispersion in KBr, the main absorption bands are as follows:

| norbornyl | 2950, 2870, 1455 cm$^{-1}$ |
|---|---|
| OH | 3200 cm$^{-1}$ |
| aromatic nucleus | 1615, 1500 cm$^{-1}$ |

N.M.R. SPECTRA

In solution in dimethyl sulfoxide the following main peaks are observed (TMS reference)

| norbornyl | CH$_2$ | 1.4 ppm | massive |
|---|---|---|---|
| | H endo | 2.35 ppm | triplet |
| OH | | 9.38 ppm | singlet |
| aromatic protons | | 6.72 – 7.15 ppm | |
| CH$_3$ | | 2.2 ppm | singlet |

EXAMPLE 10

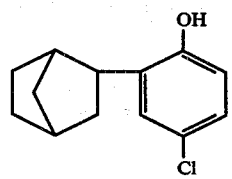

2-EXO-NONBORNYL-4-CHLOROPHENOL 120g 2-exo-norbornyl anisole (0.59 mole) and 135g phosphorus pentachloride (0.65 mole) are heated to 100° C for 2 hours, then the phosphorus trichloride formed is distilled at reduced pressure. It is then poured into iced water and extracted with chloroform. The organic phase is washed with a solution of sodium bicarbonate, then with water until neutral. After having driven off the solvent, it is distilled at reduced pressure and the fraction $B.P_{0.2} = 120°$ C is recovered. 95g of a colourless oil are thus obtained. which oil is 2-exo-norbornyl-4-chloroanisole.

4g red phosphorus, 200 cm$^3$ hydriodic acid and 400 cm$^3$ acetic acid are heated at 100° C for 30 minutes under nitrogen. After cooling to 20° C, the oil previously obtained is added and the mixture is heated to 100° – 110° C, under nitrogen for 24 hours. Filtration is then carried out on "Celite 545" and the filtrate is poured into 1 liter of water. The mixture is extracted with methylene chloride, washed in water, dried on sodium sulphate and the solvent is driven off. The product is distilled at reduced pressure and the fraction $R.P._{0.1} = 122°$ C is recovered. 55g of a colourless oil are obtained.

ANALYTIC CHARACTERISTICS

Analysis for $C_{13}H_{15}OCl$ (M.W. = 222.72)

|  |  | C | H | Cl |
|---|---|---|---|---|
| Calculated | (%) | 70.11 | 6.79 | 15.92 |
| Found | (%) | 70.20 | 6.67 | 15.83 |

I.R. SPECTRA

Recorded in the form of a film, the spectrum comprises the following characteristic bands:

| norbornyl | 2960, 2880, 1480 cm$^{-1}$ |
| OH | 3550, 3440 |
| aromatic nucleus | 1610, 1500, 815 |

N.M.R. SPECTRA

In solution in CDCl$_3$, the following peaks are observed (TMS reference):

| norbornyl | CH$_2$ | 1.5 ppm | massive |
|  | H endo | 2.8 ppm | triplet |
| OH |  | 5 ppm |  |
| aromatic protons |  | 6.65–7–7.15 ppm |  |

EXAMPLE 11

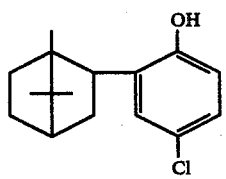

2-ISOBORNYL-4-CHLOROPHENOL 80g 2-isobornyl anisole (0.33 mole) and 76g phosphorus pentachloride (0.36 mole) are heated at 120° C for 2 hours. The PCl$_3$ formed is then distilled under vacuum and the reaction mixture is poured into iced water. The mixture is extracted with ether, the organic phase is washed with water until neutral, dried on sodium sulphate and the ether is evaporated. 90g of a red oil (2-isobornyl-4-chloroanisole) are obtained.

4g red phosphorus, 200 cm$^3$ hydriodic acid and 500 cm$^3$ acetic acid are heated under reflux for 30 minutes. After cooling to 20° C, the oil previously obtained is added and the mixture is heated under reflux, under nitrogen, for 24 hours. After cooling, the insoluble matter is separated by filtration and the filtrate is poured into 1 liter of water. The mixture is extracted with ether, washed with a solution of sodium thiosulphate and then with water until neutral. After drying on sodium sulphate, the ether is evaporated and the product is distilled at reduced pressure. The fraction $B.P._{0.1} = 150°$ C is recovered. After two crystallizations from pentane, 18g of pure product are obtained. M.P. = 86°–87° C.

ANALYTICAL CHARACTERISTICS

Analysis for $C_{16}H_{21}OCl$ (M.W. = 264.80)

|  |  | C | H | Cl |
|---|---|---|---|---|
| Calculated | (%) | 75.28 | 7.99 | 13.39 |
| Found | (%) | 72.65 | 7.86 | 13.28 |

I.R. SPECTRA

In solution in CDCl$_3$, the following characteristic bands are noted:

| isobornyl | 2960, 2860, 1480, 1460, 1380, 1370 cm$^{-1}$ |
| OH | 3600 cm$^{-1}$ |

N.M.R. SPECTRA

In CDCl$_3$, the following peaks are observed (TMS reference):

| isobornyl | CH$_3$ | bridge head | 0.75 ppm | (s) |
|  | CH$_3$ | geminal | 0.80–0.85 ppm | (s) |
|  | H | endo | 3.05 ppm | triplet |
| OH |  |  | 5 ppm |  |
| aromatic protons |  |  | 6.6–6.45–7.25 ppm |  |

EXAMPLE 12

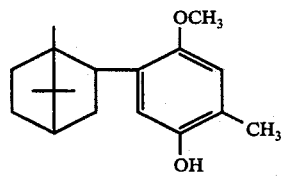

2-METHYL-4-METHOXY-5-ISOBORNYL PHENOL 19g of 85% meta-perchlorobenzoic acid are added, with stirring, at ambient temperature to a solution of 20g 2-methyl-4-methoxy-5-isobornyl benzaldehyde in 150 cm$^3$ anhydrous methylene chloride. After stirring for 30 minutes, the mixture is filtered and the filtrate is washed with a solution of sodium bicarbonate, then with a solution of sodium bisulphite and finally with water. After drying on sodium sulphate, the solvent is evaporated, the residue taken up in 150 cm$^3$ methanol 150 cm$^3$ 10N soda are added and stirring is carried out for 10 minutes after which the mixture is acidified with concentrated HCl. One extracts with methylene chloride and then washes with water until neutral. After drying on sodium sulphate and evaporation of the solvent, the residue is crystallized twice from iso-octane and 10.5g of pure product are obtained. m.p. = 120° C.

ANALYTICAL CHARACTERISTICS

Analysis for $C_{18}H_{26}O_2$ (M.W. = 274.39)

|  |  | C | H | O |
|---|---|---|---|---|
| Calculated | (%) | 78.79 | 9.55 | 11.66 |
| Found | (%) | 78.90 | 9.50 | 11.60 |

I.R. SPECTRA

In solution in $CCl_4$, the following characteristic bands are noted:

| isobornyl | 2950, 2880, 1470, 1460 $cm^{-1}$ |
|---|---|
| —O—CH$_3$— | 2830 $cm^{-1}$ |

N.M.R. SPECTRA

In solution in $CDCl_3$, the following peaks are observed (TMS reference):

| isobornyl | CH$_3$ | bridge head | 0.65 ppm | (s) |
|---|---|---|---|---|
|  | CH$_3$ | geminal | 0.80 ppm | (s) |
|  | H | endo | 3.2 ppm | triplet |
| —O—CH$_3$— |  |  | 3.72 ppm | (s) |
| OH |  |  | 4.6 ppm | (s) |
| CH$_3$ | aromatic |  | 2.2 ppm | (s) |
| H | aromatic |  | 6.55–6.7 ppm |  |

EXAMPLE 13

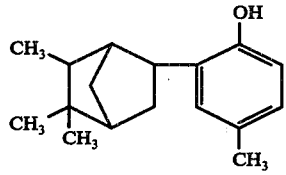

2-ISOCAMPHYL-4-METHYLPHENOL 1080g para-cresol (10 moles) and 680g camphene (5 moles) are dissolved in 2 liters of nitromethane. Whilst cooling to 0° C, there is added in small portions 450g aluminum chloride, whilst ensuring that the temperature does not exceed 5° C. It is then left for one night in the refrigerator. One then washes several times with water, dries the mixture on sodium sulphate and evaporates the nitromethane under vacuum. One then distills under reduced pressure and the fraction $B.P_3 = 160° - 165°$ C is recovered, which is crystallized from iso-octane. 210g of pure product are obtained. M.P. = 75°–76° C.

ANALYTICAL CHARACTERISTICS

Analysis for $C_{17}H_{24}O$ (M.W. = 244.36)

|  |  | C | H | O |
|---|---|---|---|---|
| Calculated | (%) | 83.55 | 9.90 | 6.55 |
| Found | (%) | 83.42 | 9.96 | 6.62 |

I.R. SPECTRA

In solution in $CCl_4$, the following bands are noted:

| isocamphyl | : | 2950, 2860, 1470, 1450, 1365, 1375 $cm^{-1}$ |
|---|---|---|
| OH | : | 3600 |

N.M.R. SPECTRA

| isocamphyl | CH$_3$ |  | 0.85 ppm |  | doublet |
|---|---|---|---|---|---|
|  | CH$_3$ | geminal | 0.87 – 1 ppm |  |  |
|  | H | endo | 2.9 ppm |  | triplet |
| CH$_3$ | aromatic |  | 2.17 ppm |  |  |
| H | aromatic |  | 6.7 – 6.85 ppm |  |  |
| OH |  |  | 8.8 ppm |  | (s) |

EXAMPLE 14

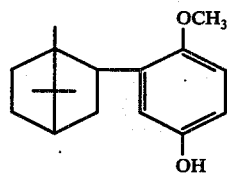

3-ISOBORNYL-4-METHOXYPHENOL 8g of 85% m-perchlorobenzoic acid are added at ambient temperature and with stirring to a solution of 8g (0.03 mole) 3-isobornyl-4-methoxy benzaldehyde in 70 $cm^3$ anhydrous methylene chloride. After stirring for 2 hours, one filters and washes the organic phase with a solution of potassium bicarbonate, then with water. After drying, the solvent is evaporated and the residue is taken up in 50 $cm^3$ methanol and 5 $cm^3$ soda lye. One leaves it in contact for 30 minutes, then acidifies with HCl, dilutes with 200 $cm^3$ water and extracts with ether. The ethereal phase is washed with water and then the ether is driven off. The residue is dissolved in benzene and the solution is poured onto a 50g silica column. One elutes with 300 $cm^3$ benzene, evaporates the solvent and crystallizes from iso-octane. 3.8g of pure product are thus obtained. M.P. = 98° – 100° C.

ANALYTICAL CHARACTERISTICS

Analysis for $C_{17}H_{24}O_2$ (M.W. = 260.36)

|  |  | C | H | O |
|---|---|---|---|---|
| Calculated | (%) | 78.42 | 9.29 | 12.29 |
| Found | (%) | 78.35 | 9.40 | 12.25 |

I.R. SPECTRA

In solution in $CCl_4$, the following bands are noted:

| isobornyl | : | 2950, 2880 $cm^{-1}$ |
|---|---|---|
| - O - CH$_3$ - | : | 2820, 1230, 1050 |
| OH | : | 3608 $cm^{-1}$ |

N.M.R. SPECTRA

In solution in CDCl$_3$, the following peaks are observed (TMS reference):

| isobornyl | CH$_3$ bridge head | 0.65 ppm (s) |
|---|---|---|
|  | CH$_3$ geminal | 0.78 ppm (s) |
| —O—CH$_3$ |  | 3.70 ppm (s) |
| OH |  | 5.42 ppm (s) |
| aromatic protons |  | 6.75 ppm (m) |

EXAMPLE 15

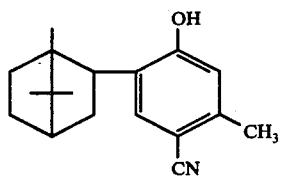

2-ISOBORNYL-4-CYANO-5-METHYLPHENOL 14.5g (0.05 mole) of 2-methyl-4-methoxy-5-isobornyl benzaldehyde are heated under reflux for 18 hours with 5g hydroxylamine hydrochloride, 6g sodium acetate and 150 cm$^3$ acetic acid. After evaporation the residue is taken up in benzene. The solution obtained is poured onto a 100g column of silica. It is eluted with 350 cm$^3$ benzene and after evaporation, 9g 2-methyl-4-methoxy-5-isobornyl benzonitrile are obtained. M.P. = 110° C.

The preceding product is heated with 90g pyridine hyrochloride for 6 hours to 220°-225° C. The mixture which is still hot is poured into 1 liter of water and the unsoluble substance formed is recovered by filtration. After washing with water and drying, one crystallizes from a benzene - iso-octane mixture (7:3) and 7.5g of pure product are thus obtained. M.P. = 200° C.

ANALYTICAL CHARACTERISTICS

Analysis for C$_{18}$ H$_{23}$ O N (M.W. = 269.37)

|  |  | C | H | N |
|---|---|---|---|---|
| Calculated | (%) | 80.25 | 8.61 | 5.20 |
| Found | (%) | 80.35 | 8.48 | 5.25 |

I.R. SPECTRA

In solution in chloroform, the following main bands are noted:

| isobornyl | : | 2960, 2880 cm$^{-1}$ |
|---|---|---|
| OH | : | 3595, 3300 cm$^{-1}$ |
| - CN | : | 2225 cm$^{-1}$ |

N.M.R. SPECTRA

In solution in a CDCl$_3$ - DMSO mixture the following peaks are observed. (TMS reference)

| isobornyl | : | CH$_3$ bridge head | 0.75 ppm | (s) |
|---|---|---|---|---|
|  | : | CH$_3$ geminal | 0.82 – 0.87 ppm | (s) |
| aromatic nucleus | : | CH$_3$ | 2.38 ppm | (s) |
| protons | : |  | 6.75 – 7.42 ppm |  |
|  | : | OH | 9.42 ppm |  |

EXAMPLE 16

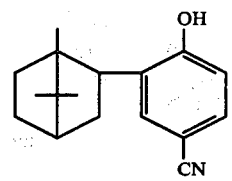

2-ISOBORNYL-4-CYANO PHENOL 9g 3-isobornyl-4-methoxy benzaldehyde (0.033 mole) are heated under reflux for 20 hours with 3g hydroxylamine hydrochloride (0.043 mole), 3g sodium acetate and 90 cm$^3$ acetic acid. The insoluble matter is separated by filtration, the solvent is evaporated and the residue taken up in several cubic centimeters of benzene and the solution is poured onto a 100g column of silica. One elutes with 400 cm$^3$ benzene, then evaporates the solvent and crystallizes the residue form iso-octane. 5.6 g of 3-isobornyl-4-methoxy benzonitrile are thus obtained. M.P. = 98° - 100° C.

The preceding product is heated under nitrogen to 220° C for 4 hours with 56g pyridine hydrochloride. The mixture, which is still hot, is poured into 300 cm$^3$ water. The insoluble matter is recovered by filtration, washed with water, dried and crystallized from a mixture of benzene and iso-octane (7:3) then from benzene. 2.1g of a pure product are obtained. M.P. = 173° C.

ANALYTICAL CHARACTERISTICS

Analysis for C$_{17}$ H$_{21}$ O N (M.W. = 355.35)

|  |  | C | H | N |
|---|---|---|---|---|
| Calculated | (%) | 79.96 | 8.29 | 5.49 |
| Found | (%) | 80.12 | 8.37 | 5.38 |

I.R. SPECTRA

In dispersion in KBr, the following main bands are noted:

| isobornyl | : | 2950, 2880 cm$^{-1}$ |
|---|---|---|
| aromatic nucleus | : | 1510, 1610, cm$^{-1}$ |
| - CN | : | 2240 cm$^{-1}$ |
| OH | : | 3260 cm$^{-1}$ |

N.M.R. SPECTRA

In solution in a CDCl$_3$ - DMSO mixture, the following peaks are observed (TMS reference)

| isobornyl | CH$_3$ bridge head | 0.74 ppm | (s) |
|---|---|---|---|
|  | CH$_3$ geminal | 0.80–0.83 ppm | (s) |
| aromatic nucleus | OH | 9.5 ppm |  |
| protons |  | 6.9–7.3–7.5 ppm |  |

BACTERIOSTATIC ACTIVITY

The bacteriostatic activity of the phenols according to the invention has been evaluated by the method of streaks in gelose media. This method comprises making increasing dilutions of the product to be tested, in nutritive geloses poured into a Petri dish.

The various bacteria to be studied are then introduced onto the geloses in parallel streaks by means of a platinum loop which has been immersed in a 24 hour old culture of each bacteria.

The bacteriostatic amount corresponds to the weakest concentration for which the bacteria does not develop along the striation.

The activity of these compounds has been studied vis a vis two gram + ve bacteria, namely *Staphylococcus Aureus* and *Streptococcus Pyrogenes*.

The following table shows the minimum inhibitory concentrations, expressed in mg/liter, of the products described in the examples.

MINIMAL INHIBITORY CONCENTRATION
mg/liter

| Product of example | *Staphylococcus Aureus* | *Streptococcus Pyrogenes* | *Escherichia Coli* |
| --- | --- | --- | --- |
| 1  | 1   | 7.5 |     |
| 2  | 5   | 15  |     |
| 3  | 1   | 5   |     |
| 4  | 2   | 30  |     |
| 5  | 5   | 10  |     |
| 6  | 2.5 | 5   |     |
| 7  | 2.5 | 5   |     |
| 8  | 7.5 | 20  | 7.5 |
| 9  | 5   |     | 20  |
| 10 | 5   |     | 10  |
| 11 | 2.5 | 10  |     |
| 12 | 5   |     |     |
| 13 | 5   | 20  |     |
| 14 | 5   | 10  |     |
| 15 | 5   | 10  |     |
| 16 | 5   | 7.5 |     |

TOXICITY

The LD 50 of the compounds of the invention, determined in the mouse and rat is greater than 1000 mg/kg.

The products according to the invention may be used as anti-infectious agents. To this end, they may be made in a suitable form for oral or rectal administration, such as tablets, capsules, suppositories having a dose of 100 – 200 mg active ingredient to be administered at the rate of 200 mg – 1,000 mg. per day.

What is claimed is:

1. A terpenophenol of formula

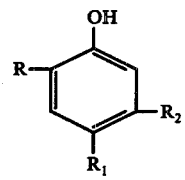

in which R is 2-exonorbornyl, $R_2$ is H or methyl and $R_1$ is chlorine or bromine.

2. A terpenophenol according to claim 1 which is 2-exo-norbornyl-4-bromo-5-methylphenol.

3. A terpenophenol according to claim 1 which is 2-exo-norbornyl-4-bromophenol.

4. A terpenophenol according to claim 1 which is 2-exo-norbornyl-4-chlorophenol.

* * * * *